United States Patent [19]

Burton

[11] 4,222,377

[45] Sep. 16, 1980

[54] PRESSURE REGULATED ARTIFICIAL SPHINCTER SYSTEMS

[75] Inventor: John H. Burton, Minneapolis, Minn.

[73] Assignee: American Medical Systems, Inc., Golden Valley, Minn.

[21] Appl. No.: 810,050

[22] Filed: Jun. 27, 1977

Related U.S. Application Data

[63] Continuation of Ser. No. 581,800, May 29, 1975, abandoned.

[51] Int. Cl.² ............................................. A61B 17/00
[52] U.S. Cl. ................................... 128/1 R; 128/325; 128/346; 128/DIG. 25
[58] Field of Search .................... 128/1 R, 346, 349 B, 128/349 BV, DIG. 25; 3/1

[56] References Cited

U.S. PATENT DOCUMENTS

| | | | |
|---|---|---|---|
| 2,455,859 | 12/1948 | Foley | 128/346 |
| 2,533,924 | 12/1950 | Foley | 128/346 |
| 3,538,917 | 11/1970 | Secker | 128/346 X |
| 3,642,005 | 2/1972 | McGinnis | 128/349 B |
| 3,720,200 | 3/1973 | Laird | 128/349 BV |
| 3,744,063 | 7/1973 | McWhorter et al. | 128/1 R |
| 3,750,194 | 8/1973 | Summers | 128/1 R X |
| 3,853,122 | 12/1974 | Strauch et al. | 3/1 X |
| 3,863,622 | 2/1975 | Buuck | 128/1 R |

OTHER PUBLICATIONS

Kintzonidis et al., Trans. Amer. Soc. Artif. Organs, 1971, vol. XVII, pp. 138, 140, 142.
Timm et al., IEEE Trans. on Bio-Med. Eng., Oct. 1970, vol. 17, No. 4, p. 352.

*Primary Examiner*—Dalton L. Truluck
*Assistant Examiner*—J. L. Krutor

*Attorney, Agent, or Firm*—Williamson, Bains, Moore & Hansen

[57] ABSTRACT

Pressure-regulated artificial sphincter apparatus for controlling vesicular incontinence is disclosed herein. The apparatus preferably comprises a generally toroidal cuff member for constricting a vessel to be opened and closed in response to fluid pressure, a squeezable fluid supply pump bulb in communication with the cuff, and a fluid pressure regulator for maintaining substantially constant fluid pressure within the cuff. The pressure regulator preferably comprises a variable volume, distensible balloon which is in fluid flow communication with the cuff. Check valve means are provided to maintain correct fluid flow throughout the apparatus. One form of this invention includes a low pressure fluid reservoir interconnected with the fluid supply bulb. Another form of this invention includes pump means for deflating the cuff by manually transferring fluid therefrom into the balloon and a restricted flow passageway extending between the balloon and the cuff to reinflate the cuff after a predetermined time to automatically occlude the affected vessel. A fluid transfer bulb described and claimed herein for use with artificial sphincter systems includes an interiorly-located, restricted flow passageway for automatic actuation of a fluid pressure responsive element.

A method for treating incontinence described herein includes the steps of surgically mounting an inflatable cuff on the vessel to be artificially opened and closed, implanting a fluid source in fluid flow communication with the cuff at another location within the animal body, and locating a pressure regulator at another location within the body for maintaining substantially constant cuff fluid pressure. A method for automatically reinflating a cuff member is also set forth herein.

4 Claims, 7 Drawing Figures

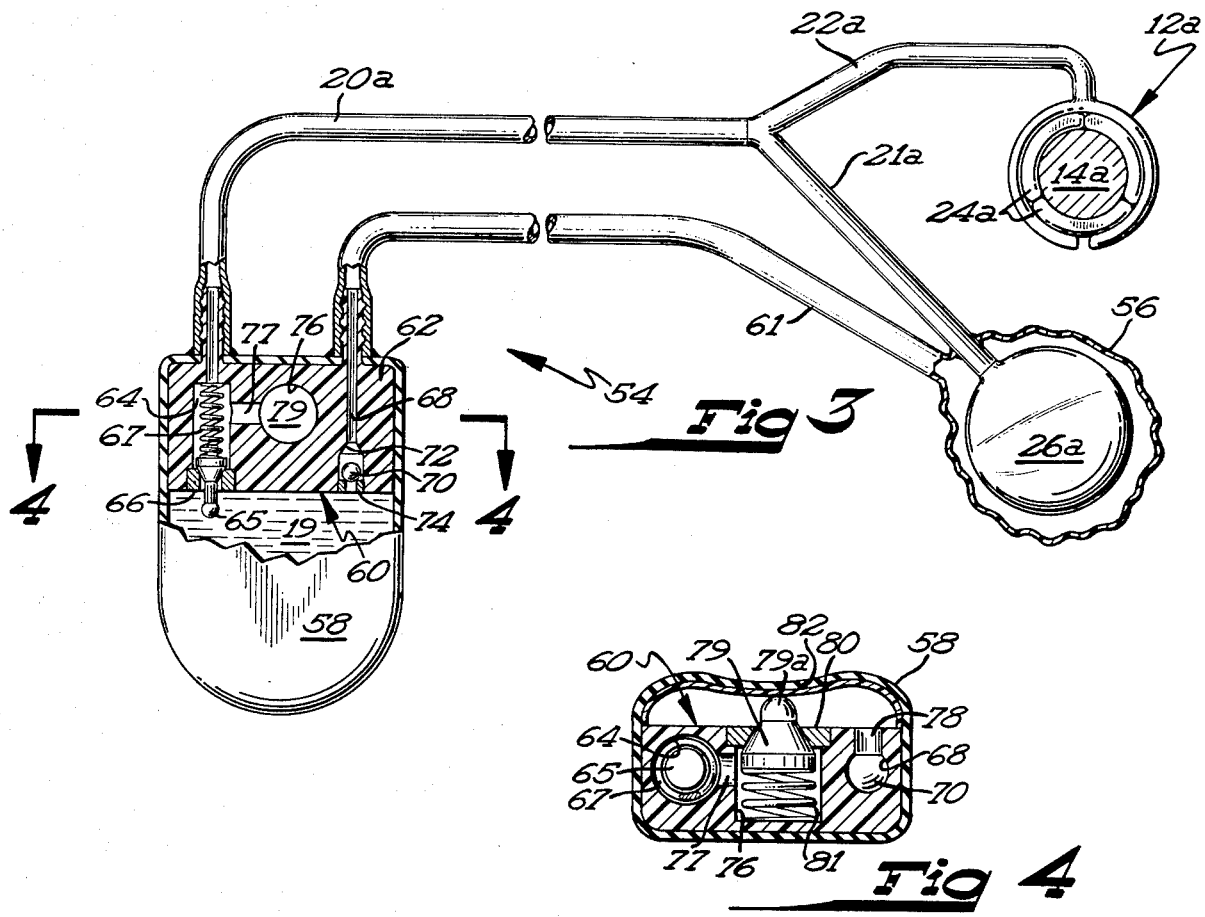
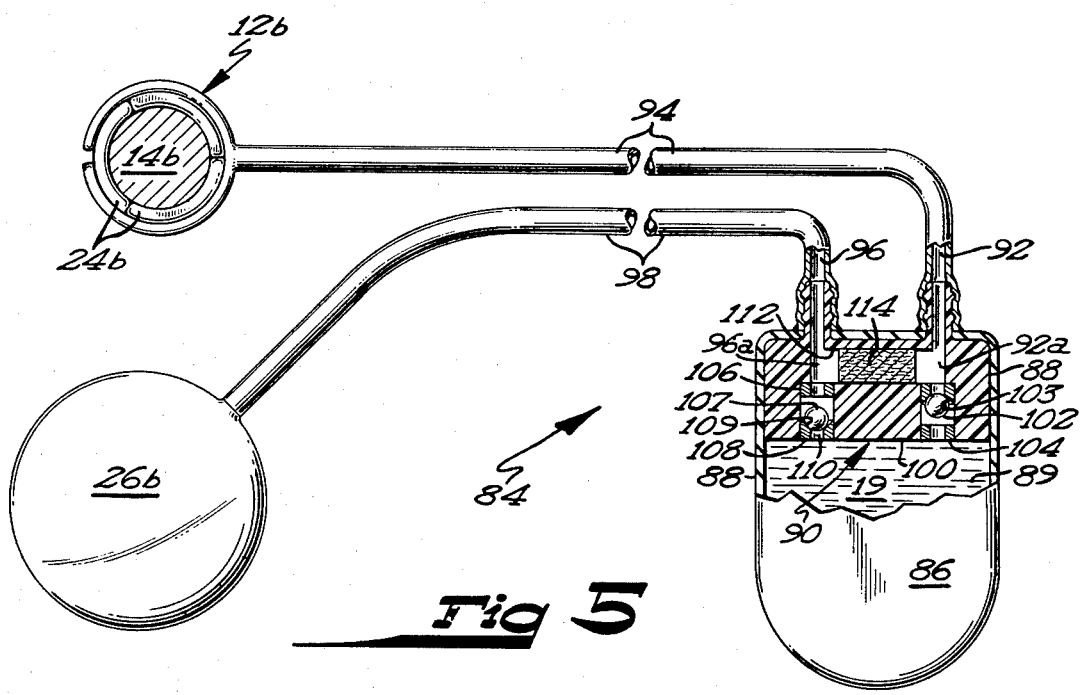

PRESSURE REGULATED ARTIFICIAL SPHINCTER SYSTEMS

This is a continuation of application Ser. NO. 581,800, filed May 29, 1975, now abandoned.

BACKGROUND OF THE INVENTION

This invention relates generally to the treatment of incontinence. More particularly, the instant invention is related to artificial sphincter systems and associated method for returning volitional control of excretory vessels to the patient.

Sphincter muscles are utilized by the body to close various duct tubes or orifices. The sphincter muscle encircles or surrounds its associated duct tube so that contraction of the sphincter will constrict the passageway. Urethral sphincter muscles, for example, preferably volitionally open and close the urethra during micturition. Where sphincter muscles or their associated nerves and fibers become inoperative because of disease or damage the unfortunate problem of incontinence will result. A plurality of prior art artificial mechanisms have been developed in an attempt to solve the problem of incontinence. Most of these devices function by intermittently occluding the affected vessel.

Artificial sphincter mechanisms for exteriorly controlling incontinence are shown in U.S. Pat. No's. 2,455,859 and 2,533,924 issued to F. E. Foley on Dec. 7, 1948 and Dec. 12, 1950, respectively. The latter two references are directed towards apparatus for controlling incontinence in males by exteriorly clamping the urethra. As described in the latter two patents, the exteriorly operable Cunningham clamp represents a now-outdated approach for controlling incontinence.

Surgically implantable devices for controlling incontinence are shown generally in U.S. Pat. No. 3,750,194 issued to G. D. Summers on Aug. 7, 1973, U.S. Pat. No. 3,744,063 issued to McWhorter et al on July 10, 1973 and U.S. Pat. No. 3,863,622 issued to R. E. Buuck on Feb. 4, 1975. The latter patents generally disclose apparatus comprising a circular cuff member responsive to fluid pressure for intermittently occluding a vessel, at least one source of fluid pressure interconnected to the cuff, and one or more interconnected valves, tubes, reservoirs or the like. An informative article related to the latter art and entitled "Intermittent Occlusion System" was published in *IEEE Transactions on Bio-Medical Engineering*, October 1970, Volume 17, No. 4, page 352. U.S. Pat. No. 3,538,917 issued to R. G. Selker on Nov. 10, 1970, illustrates an occlusion clip for selectively blocking flow through a vessel which includes an expandable, pressure-responsive member which proximally circumscribes the indicated vessel. U.S. Pat. No. 3,853,122 shows a delay means.

While the aforementioned implantable devices represent a significant improvement over earlier external clamping techniques, they are not without certain disadvantages. Prior art implantable sphincters may become disengaged in repsonse to bladder spasms or other external forces which tend to force pressurizing fluid out of the vessel-constricting cuff. In a urethral incontinence system for example, reduced cuff pressure may result in involuntary passage of urine. Another problem associated with certain prior art implantable sphincter systems is that the cuff inflation means utilized therewith may produce excessive pressure conditions which can lead to tissue damage. For example, where a prior art inflatable sphincter member has been implanted tissue damage may result unless fluid can be at least temporarily displaced from the cuff member in response to vacillating external forces on the urethra. Known prior art sphincters must be volitionally manipulated each time the affected vessel is to be either opened or closed

SUMMARY OF THE INVENTION

The incontinence control apparatus disclosed herein is adapted to be surgically implanted interiorly of an animal body and is capable of being controlled exteriorly by simply pressing the skin.

In one form of this invention the artificial sphincter apparatus comprises an inflatable cuff which circumscribes a vessel to be opened and closed and proximally engages the vessel to constrict same in response to fluid pressure, a source of fluid which is preferably connected to the cuff through a one-way check valve, and a fluid pressure regulator in fluid flow communication with the cuff which maintains substantially constant fluid pressure within the cuff to minimize tissue damage. The fluid source preferably comprises a squeezable, elastometric bulb which is adapted to be placed inneradjacent the skin for external manipulation thereof. Pressure regulation is provided by a variable volume chamber which expands and contracts in response to varying fluid pressure within the cuff. The variable volume chamber preferably comprises a deformable balloon which absorbs that volume of fluid in excess of the volume of fluid outputted by the source required to maintain a predetermined fluid pressure within the cuff. Since the pressure regulator balloon prevents overinflation of the cuff member harmful overconstruction of the affected vessel is obviated. Likewise, when cuff fluid pressure might otheriwse tend to go low, the regulator maintains continence by preserving the desired cuff fluid pressure. A releasable valve integral with the fluid source may be depressed to deflate the cuff when the vessel is to be opened.

In an alternate embodiment of this invention the sphincter apparatus comprises a low pressure fluid reservoir which is interconnected with a deformable squeeze pump. Manipulation of the pump delivers fluid from the reservoir into a cuff (which is similar to that previously described) and an associated pressure regulator for controllably occluding an affected vessel. Cooperating valve means are provided within the pump to properly direct fluid flow. The pump also includes a manually depressible release valve for volitionally opening the affected vessel by transferring fluid from the cuff (and the associated pressure regulator) back into the fluid reservoir. The fluid pressure regulator is preferabl located interiorly of the reservoir to effectively isolate the regulator from contact with the body fluids.

In an alternative embodiment the vesicular occluding cuff and its associated variable volume pressure regulator are interconnected via a unique squeezable pump bulb. Manipulation of the latter pump bulb transfers fluid from the cuff into the variable volume device, thereby deflating the cuff and opening the vessel so that body fluids may pass therethrough. The pump bulb is provided with check valve means for properly directing the fluid in response to rapid squeezing. Importantly, however, a flow bypass path is included to facilitate gradual, automatic transfer of fluid from the variable volume chamber into the cuff to slowly occlude the affected vessel. The latter path is preferably provided through a constricted passageway within the pump bulb. Thus the cuff fills automatically in response to fluid pressure provided by the variable volume chamber, and manipulation of a separate valve is obviated.

One method of treating incontinence described herein is initiated by surgically implanting an inflatable cuff in circumscribing, proximal engagement with the vessel to be opened and closed. A preferably squeezable source of fluid interconnected with the cuff is located at a location within the animal body inneradjacent the skin so that it may be squeezably manipulated from outside the body to fill the cuff. Importantly, a fluid pressure regulator is located at still another location within the animal body and placed in fluid flow communication with the cuff member. The pressure regulator preferably comprises a physiologically inert, distensible balloon member which will expand and contract in response to cuff fluid pressure. In a preferred form of this method, a one-way check valve is housed within the fluid source and interconnected between the fluid source and the expansible cuff to facilitate filling of the cuff. The source must be positioned such that a release member associated with the valve may be externally manipulated through the skin to open the affected vessel by deflating the cuff (and the pressure regulator). A similar method disclosed here preferably employs a fluid reservoir having the pressure regulator disposed therein and a squeezable pump for transferring fluid between the cuff (and associated pressure regulator) and reservoir.

Another method disclosed herein involves surgical implantation of an inflatable cuff, a variable-volume fluid reservoir, and a squeezable pump for transferring fluid therebetween. With the latter method the cuff is deflated by squeezing the pump, and displaced fluid is stored within the expansible chamber. Importantly, a restricted passageway extending between the chamber and the cuff facilitates gradual passage of fluid from the chamber into the cuff to automatically inflate same to occlude the affected vessel. The latter method preferably includes the step of locating the restricted passageway within the squeezable pump.

Thus, an important object of this invention is to provide artificial sphincter apparatus which will minimize the possibility of tissue damage. The important fluid pressure regulation feature of this invention obviates unwanted pressure excesses which might otherwise occur.

Another object of this invention is to provide implantable sphincter apparatus which may be exteriorly operated by the patient through the skin. It is a feature of this invention that the fluid pump utilized thereby is adapted to be located inneradjacent the skin for external manipulation.

Still another object of this invention is to provide sphincter apparatus of the character described which will closely approximate the functioning of natural micturition.

Yet another object of this invention is to provide sphincter apparatus which will enable predetermined physical activities by the patient. An important result of the fluid pressure regulator apparatus incorporated in the instant invention is that overconstriction of the affected vessel is obviated. Thus, bending and stressed forces incurred by the affected vessel during exercise periods will therefore not cause pressure buildup within the cuff and the resultant tissue damage associated therewith. Alternatively, decreases in cuff pressure caused by bending or twisting forces will be remedied by the fluid pressure regulating means to prevent embarrassng or unwanted fluid passage through the affected vessel.

Still another object of this invention is to provide sphincter apparatus of the character described which will not be affected by bladder spasms or external forces experienced by the cuff. The latter characteristics make the instant apparatus ideally suited for treatment of urinary incontinence.

Another object of this invention is to provide sphincter apparatus of the character described which will predictably maintain cuff pressure within predetermined, known limits.

Yet another important object of this invention is to provide artificial sphincter apparatus which requires only minimal patient manipulation for operation. One important form of this invention is characterized by automatic cuff inflation.

A still further object is to provide a pump bulb for use with artificial sphincter systems which facilitates automatic inflation of a desired element of the apparatus.

A further object of this invention is to provide methods for treating incontinence. Importantly, the methods disclosed herein are characterized by automatic maintenance of predetermined cuff pressure.

These and other objects of this invention, together with features of novelty appurtenant thereto, will appear or become apparent in the course of the following detailed description.

BRIEF DESCRIPTION OF THE DRAWINGS

In the following drawings, which form a part of the specification and are to be construed in conjunction therewith, and in which like reference numerals have been employed to indicate like parts in the various views:

FIG. 3 is a pictorialview of a pressure-regulated artificial sphincter system including a low pressure reservoir, with parts thereof broken away or shown in section for clarity;

FIG. 4 is a sectional view of the pump bulb valve structure taken along line 4—4 of FIG. 3 showing the sealed upper chamber therein;

FIG. 5 is a pictorial view of a pressure-regulated artificial sphincter system characterized by automatic cuff inflation, and with parts thereof broken away or shown in section for clarity;

DETAILED DESCRIPTION OF THE DRAWINGS

Figure 1:
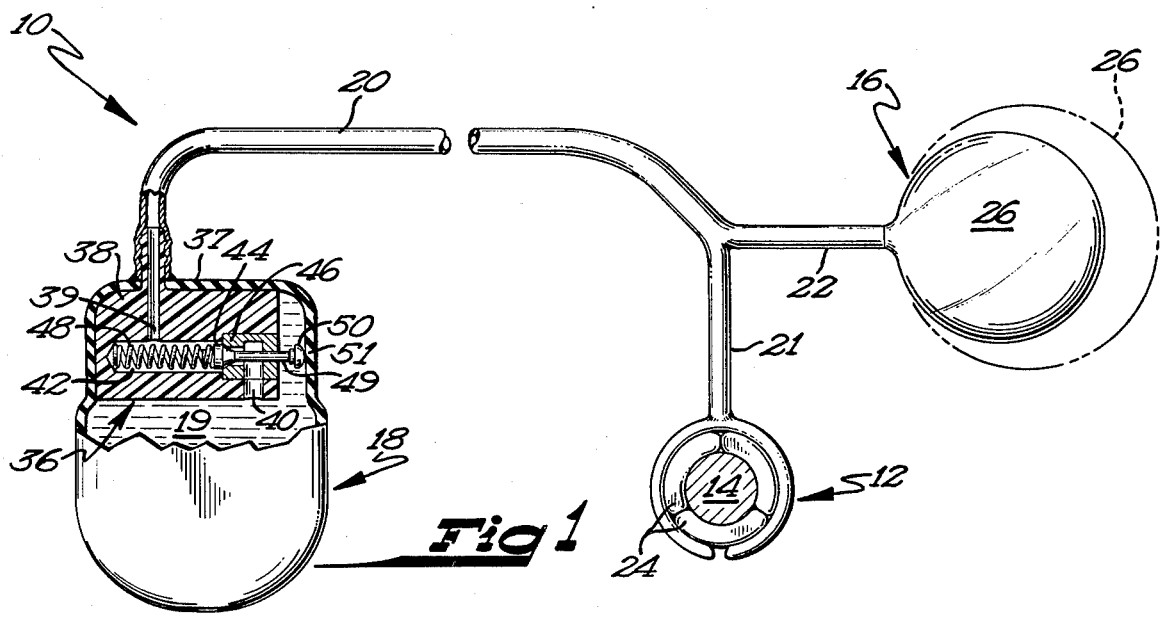
FIG. 1 is a pictorial view of a pressure-regulated artificial sphincter system constructed in accordance with the teachings of this invention with parts thereof broken away or shown in section for clarity.

Referring initially to FIG. 1, a pressure-regulated artificial sphincter system 10 comprises a generally circular cuff member 12 which encircles an affected vessel 14, a variable volume chamber 16 which regulates system fluid pressure, and a preferably manually actuable pump 18 which contains a physiologically inert fluid 19. Cuff 12 receives fluid 19 from pump 18 through a pair of physiologically inert, tubular plastic hoses 20 and 21. Similarly, pressure regulator 16 receives fluid through hoses 20 and 22. The system 10 is activated by squeezing pump 18 thereby forcing fluid into cuff 12 and regulator 16.

Cuff 12 includes a deformable membrane or wall portion 24 which proximally circumscribes vessel 14. As cuff fluid input pressure increases membrane 24 will expand and thereby occlude vessel 14. The cuff will be discussed in more detail later in conjunction with FIG. 7. The cuff is shown and described in U.S. Pat. No. 3,863,622 issued to R. E. Buuck on Feb. 4, 1975, which is hereby incorporated by reference. Importantly, the cuff members employed in each of the embodiments shown in FIGS. 1, 3 and 5 are identical.

The variable volume chamber 16 preferably comprises a distensible balloon member 26. Balloon 26 is preferably comprised of physiologically inert elastomer. The balloons employed by the embodiments of FIGS. 1, 3 and 5 are identical.

Figure 2:
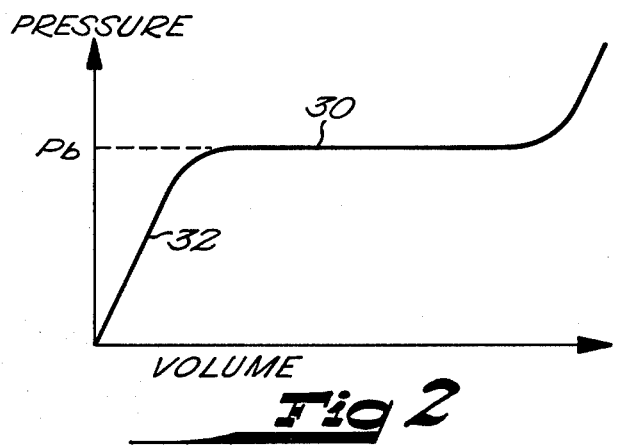
FIG. 2 graphically depicts the general relationship between the volume of fluid inputted to the pressure regulator and the corresponding fluid pressure therewithin.

As fluid enters balloon 26 and cuff 12 vessel 14 will become constricted in response to expansion of member 24. Pressure will gradually rise until a predetermined pressure $p_b$ (FIG. 2) is reached. At this time balloon 26 will expand and substantially maintain the pressure within member 24 (and tubes 20, 21 and 22) equal to pressure $p_b$. Balloon 26 thus displaces a volume of fluid in excess of the amount necessary to maintain pressure $p_b$ in the cuff 12, and in so doing it will eventually occupy the larger diameter volume indicated by dotted lines (FIG. 1). A portion 30 of the graphical pressure-volume trace shown in FIG. 2 represents the pressure regulator characteristics of the balloon. The relatively small slope of this segment indicates that fluid pressure within the balloon (and the cuff) is substantially constant. As will be described in more detail later, fluid backflow into the pump 18 is prevented at this time. Initial filling of balloon 26 is generally indicated by graphical segment 32 (FIG. 2).

The fluid source 18 preferably comprises a deformable elastometric bulb 34 which sealably encloses fluid 19 and a releasable check valve assembly 36.

Check valve 36 preferably comprises a rigid, plastic cube 38 in which a plurality of passageways have been provided. A first passageway 39 receives hose 20. A second passageway 40 is in communication with fluid 19 interiorly of the bulb. A generally cylindrical, transverse passageway 42 extends between passageways 39 and 40 to interconnected same. Passageway 42 contains a funnel shaped, tapered poppet plug 44, a similarly tapered, resilient toroidal valve seat 46, and a coiled spring 48 which normally biases plug 44 towards to block passageway 42. When bulb 34 is squeezed, the resulting increased fluid pressure at orifice 40 will be sufficient to deflect plug 44 leftwardly (as viewed in FIG. 1) thereby exposing an orifice in seat 46 and thereby opening the valve. When the squeeze bulb is released spring 48 will urge plug 44 into engagement with seat 46 to prevent fluid backflow by blocking passageway 42. The bulb can thus be released after filling cuff 12 without fear of inadvertent cuff deflation.

Valve assembly 36 is adapted to be manually released to deflate cuff 12 and thereby open the affected vessel 14. Plug 44 includes an elongated, cylindrical release stem 49 which extends through the orifice within seat 46 and exits from cube 38. A tip portion 50 of release 49 may be contacted by depressing bulb side wall portion 51, such that plug 44 is moved toward the left (as viewed in FIG. 1) against predetermined tension from spring 48. When fluid is thereby transferred back into bulb 34 the vessel 14 will become unblocked.

As various vibrations or shock forces are experienced by vessel 14 deformable cuff portion 24 will experience slight deformation. However, the buildup of fluid pressure within the cuff in response to deformation thereof will be prevented by deformable balloon 26. Balloon 26 will maintain substantially constant fluid pressure by absorbing that volume of fluid in excess of the amount of fluid necessary to maintain a predetermined cuff pressure. The instant apparatus will thus constrict the affected vessel to maintain continence while obviating harmfull cuff pressure excesses. The pressure regulating affect of the balloon will also prevent sudden pressure drops within the cuff which might occur, for example, during moderate physical activities. Thus inadvertent or embarrassing excretion through the vessel 14 will be obviated.

A slightly modified artificial sphincter system 54 is shown in FIG. 3. System 54 preferably comprises a toroidal cuff member 12a, a distensible balloon member 26a for regulating fluid pressure, a low pressure fluid reservoir 56, and a squeezable pump bulb 58 for distributing fluid from reservoir 56 to balloon 26a and cuff member 12a. Cuff 12a is identical to cuff 12, and it comprises an expansible wall portion 24a which proximally surrounds a vessel 14a which is to be opened and closed. Balloon 26a is identical to balloon 26. Unlike pump bulb 34, however, pump bulb 58 is adapted to be squeezed several times to transfer fluid throughout the system 54. For the latter purpose a valve assembly 60 (FIGS. 3 and 4) is included within the upper confines of the bulb 58.

Reservoir 56 preferably comprises a physiologically inert, deformable volume which surrounds and encloses balloon 26a. Reservoir 56 is in fluid flow communication with bulb 58 through a tubular hose 61, which is sealably received within valve assembly 60. It is apparent that in the event of failure or rupture of balloon 26a its contents will be confined within the reservoir 56. Alternatively bulb 26a can be located externally of the reservoir.

Valve assembly 60 is adapted to direct fluid from reservoir 56 to the cuff and balloon regulator in response to multiple squeezing of bulb 58. Valve assembly 60 also facilitates manual transference of fluid out of cuff 12a (and regulator 26a) and back into reservoir 56. Assembly 60 comprises a generally cubical frame block 62 in which a plurality of passageways have been formed by drilling or the like. Block 62 is preferably adhesively secured to the upper wall portions interiorly of the bulb 58.

Passageway 64 contains a funnel-shaped poppet plug 65, a similarly tapered toroidal valve seat 66, and a spring 67 which biases the plug 65 into engagement with seat 66 to normally block passageway 64. A passageway 68 which communicates with reservoir 56 via hose 61 contains another check valve comprised of a spherical plug 70, a smaller diameter tapered valve seat 72, and a retainer orifice 74 which maintains plug 70 within passsageway 68. Each time bulb 58 is squeezed, plug 65 will become dislodged and fluid will be outputted through passageway 64 into hose 20a, thereby filling cuff 12a and regulator 26a. Each time bulb 58 is subsesquently released, passageway 64 will become blocked, passageway 68 will open, and fluid within reservoir 56 will be sucked into the bulb. the increasng fluid output pressure will occlude vessel 14a by expanding cuff portion 24a in the manner previously described. Cuff fluid pressure will be limited to a pressure $p_b$ (FIG. 1) by regulator 26a.

When it is desired to open vessel 14a, cuff 12a (and balloon regulator 26a) are deflated by draining fluid therein back into reservoir 56. A separate passageway 76 (FIG. 4) is provided to manually transfer fluid from passageway 64 into passageway 68. Passageway 76 communicates with passageway 64 through an orifice 77, and with passageway 68 through an orifice 78. Passageway 76 includes a funnel shaped poppet plug 79, a similarly tapered toroidal valve seat 80, and a preferably coiled spring 81 which normally biases plug 79 into releasable engagement with seat 80 to selectively block passageway 76. The upper plug end 79a interiorly abuts bulb wall portion 82 so that plug 79 may be manually depressed by squeezing the bulb near the upper portion thereof. When plug 79 is depressed, fluid pressure within regulator 26a and cuff 12a will force fluid back into reservoir 56 through hose 61. Afterwards the cycle may be repeated by again squeezing bulb 58 to reinflate the cuff (and balloon regulator 26a) in the manner previously described.

The artificial sphincter apparatus 84 (FIG. 5) also includes a variable volume balloon regulator 26b and a cuff 12b for occluding a circumscribed vessel 14b. A preferably squeezeable, elastomatic pump bulb 86 directs fluid 19 between regulator 26b and cuff 12b. Unlike the previously described embodiments however, apparatus 84 is adapted to automatically inflate associated cuff member 12b after a predetermined time. In response to squeezing bulb 86 will deflate cuff 12b to thereby temporarily open the affected vessel 14b.

The preferably elastic bulb wall 88 encloses a fluid containing space 89 and a valve assembly 90, which is adhesively secured within the upper confines of bulb 86. Bulb 86 includes a first fluid passageway 92 which communicates with cuff 12b through a hose 94, and a second fluid passageway 96 which communicates with regulator 26b through a similar tubular hose 98.

Pump bulb 86 is adapted to transfer fluid from cuff 12b into balloon means 26b in response to squeezing thereof. Thus, unlike the previously described embodiments, squeezing of bulb 86 will open the affected vessel 14b. Valve assembly 90 facilitates fluid transfer by properly directing fluid. Assembly 90 includes a cubical frame 100 in which a plurality of passageways are defined by drilling or the like. A first valve passageway 92a (in fluid flow communication with passageway 92) is intermittently closed by a check valve comprised of spherical plug 102, tapered valve seat 103, and plug retaining insert 104. One-way fluid transfer from passageway 92 into space 89 is thereby facilitated in response to bulb suction. A similar valve passageway 96a (which communicates with passageway 96) has a oneway check valve comprised of a retainer insert 106, a spherical plug 107, and a toroidal valve seat 108. Seat 108 has an upper, tapered shoulder portion 109 and a central orifice 110 which communicates with space 89./ Thus one-way transfer of fluid from space 89 through passageways 110, 96a and 96 occurs in response to squeezing of the bulb 86. In this manner fluid is transferred from the cuff 12b into the distensible balloon regulator 26b, which expands in response thereto while maintaing substantially constant pressure (FIG. 2).

Importantly, a flow bypass resistance passageway 112 interconnects passageways 96a and 96 with passageways 92a and 92. Fluid flow through passageway 112, however, is impeded by a restriction 114, which preferably comprises glass filter material having a diameter substantially the same as passageway 112. In response to the predetermined pressure within regulator 26b, fluid will gradually be transferred through restricted passageway 112 and into cuff 12b to inflate portion 24b thereof. Thus vessel 14b will gradually be occluded by the delayed passage of fluid enabled by the flow resistive passageway 112. The cuff portion 24b is thus automatically inflated after a predetermined time to occlude passageway 14b without additional manipulation by the patient. As in the case of the previously discussed embodiments, the balloon regulator means will substantially maintain an equilibrium pressure of $p_b$ (FIG. 2).

Figure 6:
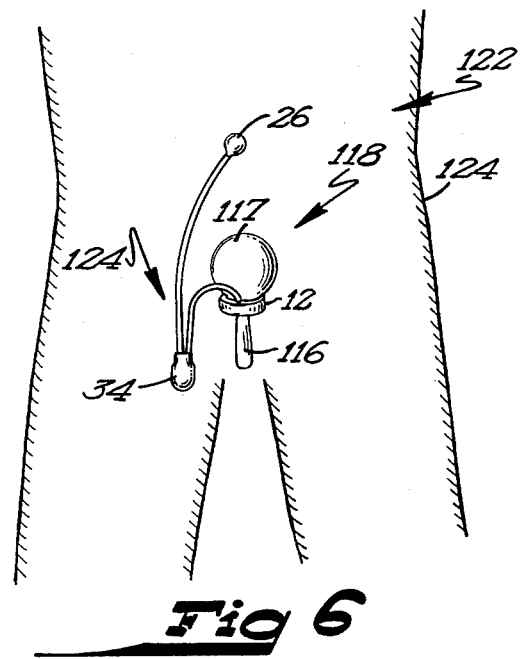
FIG. 6 is an abbreviated sectional view of a human torso showing the preferred location of the sphincter system shown in FIG. 1; and, FIG. 7 is a perspective view illustrating a cuff member in proper position on an affected vessel which is to be artifically opened and closed.

Each of the previously described artificial sphincter embodiments is adapted to be surgically implanted completely within an animal body. In FIG. 6 the sphincter apparatus 10 has been installed within a human torso to remedy urinary incontinence by providing a substitute for a defective urethral sphincter muscle. Cuff 12 circumscribes urethra 116 which extends from the bladder 117. The balloon regulator 26 is located within the peritoneal cavity 118, and squeeze pump 34 is preferably located within the scrotum (or labia in the case of a female).

Figure 7:
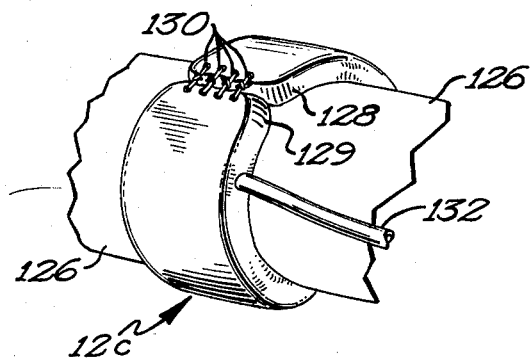

In each case the sphincter apparatus is implanted within the trunk 122 by first makingg an abdominal incision through the skin 124 overlying the pelvic cavity 125. After the urethra 116 is exposed, the cuff member is implanted around it by a prior art wrapping procedure in which the cuff ends are tied together. As best shown in FIG. 7, the cuff 12c is folded around a vessel 126 and preferably fastened thereto by tying cuff ends 128 and 129 together with a plurality of sutures 130. The fluid supply tube 132 is then carefully routed toward the desired fluid source. The latter procedure is discussed generally in U.S. Pat. No. 3,863,622 which is hereby incorporated by reference.

In each case the pump bulb is located so that it may be externally manipulated by pressing it through the skin. In the case of systems 10 and 54 the squeeze bulb must be positioned such that valve portions 50 and 79a, respectively, may also be actuated through the skin.

It should be apparent that the instant invention is of equal utility in treating males or females. Because fluid flow is limited to a closed system operative reliability is enhanced. Fluid pressure maintenance provided by the balloon regulator in part obviates the need for a plurality of check valves otherwise employed by some prior art devices. Notwithstanding the operative reliability of the apparatus, it is preferable to include a radio-opaque dye within the physiologically inert liquid 19 is utilized by the apparatus. In the rare event that problems later develop the dye enables investigation with conventional X ray techniques.

What is claimed is:

1. An artificial sphincter system for reversibly occluding a passageway, said system comprising:
    inflatable cuff means substantially encircling a vessel to be opened and closed for constricting said vessel in response to fluid pressure;

means for supplying fluid under pressure comprisingg a manually deformable, elastomeric bulb in fluid flow configuration with said cuff means, said bulb serving as both a fluid reservoir and a pump;

variable volume chamber means in fluid flow communication with the inside of said cuff means for regulating fluid pressure therein by expanding and contracting in response to fluid pressure;

unrestricted flow passage means connecting said supplying means with both the inside of said cuff means and said variable volume chamber;

check valve means housed within said elastomeric bulb for normally allowing one way passage of fluid from said supplying means simultaneoulsy to said cuff means and said variable volume chamber means through said flow passage means; and manually operable release means operatively associated with said check valve means for deflating said cuff means and said variable volume chamber means by selectively permitting fluid to flow from said cuff means and said variable volume chamber means back through said passage means to said elastomeric bulb, fluid being transferable simultaneously into said cuff means and said variable volume chamber means by squeezing said bulb, and said manually operable release means being disposed within said elastomeric bulb adjacent a side wall thereof whereby manipulation of said side wall operates said release means to open said check valve.

2. The combination as in claim 1 wherein said variable volume chamber means comprises a distensible balloon.

3. The combination as in claim 1 wherein said cuff means comprises an expansible wall portion in proximal engagement with said vessel.

4. The combination as defined in claim 1 wherein said flow passage means comprises a first fluid line connected to said supplying means and a pair of branch lines separately connected between said first fluid line and said cuff means and said variable volume chamber means, thereby placing said supplying means, said cuff means and said variable volume chamber means in fluid flow communication with each her.

* * * * *